United States Patent
Nelson et al.

(10) Patent No.: US 10,047,030 B2
(45) Date of Patent: Aug. 14, 2018

(54) COATING TO INHIBIT FOULING OF REACTORS FOR CUMENE HYDROPEROXIDE CLEAVAGE

(71) Applicant: SABIC GLOBAL TECHNOLOGIES B.V., Bergen op Zoom (NL)

(72) Inventors: Mark Erik Nelson, Mt. Vernon, IN (US); Arkady Samuilovich Dykman, St. Petersburg (RU); Andrey Vladimirovich Zinenkov, St. Petersburg (RU)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 15/501,184

(22) PCT Filed: Aug. 7, 2015

(86) PCT No.: PCT/IB2015/056023
§ 371 (c)(1),
(2) Date: Feb. 2, 2017

(87) PCT Pub. No.: WO2016/020895
PCT Pub. Date: Feb. 11, 2016

(65) Prior Publication Data
US 2017/0226036 A1    Aug. 10, 2017

(30) Foreign Application Priority Data

Aug. 8, 2014  (RU) ................................ 2014132768

(51) Int. Cl.
*C07C 37/08* (2006.01)
*C07C 45/53* (2006.01)
*B01J 19/02* (2006.01)

(52) U.S. Cl.
CPC ............... *C07C 45/53* (2013.01); *B01J 19/02* (2013.01); *C07C 37/08* (2013.01); *B01J 2219/0245* (2013.01)

(58) Field of Classification Search
CPC ........... C07C 56/53; C07C 37/08; B01J 19/02
See application file for complete search history.

(56) References Cited

U.S. PATENT DOCUMENTS

| 4,322,560 A | 3/1982 | Vaughan |
| 6,057,483 A | 5/2000 | Zakoshansky et al. |
| 8,722,941 B2 | 5/2014 | Bellenger et al. |

FOREIGN PATENT DOCUMENTS

WO    0014042 A1    3/2000

OTHER PUBLICATIONS

"High Performance Fluoropolymer Coatings & Linings," Solva Solexis, Jan. 1, 2006; pp. 1-16.
International Search Report for International Application No. PCT/IB2015/056023; International Filing Date: Aug. 7, 2015; dated Nov. 18, 2015; 6 Pages.
Written Opinion of the International Searching Authority for International Application No. PCT/IB2015/056023; International Filing Date: Aug. 7, 2015; dated Nov. 18, 2015; 7 Pages.

*Primary Examiner* — Sikarl A Witherspoon
(74) *Attorney, Agent, or Firm* — Cantor Colburn LLP

(57) ABSTRACT

The disclosure concerns methods comprising forming a phenol and acetone mixture from decomposition of a cumene hydroperoxide or a phenol, acetone, and AMS from the decomposition of a mixture containing dicumyl peroxide in a system comprising one or more reactors where at least a portion of an inner surface of the one or more reactors has a polymer coating and wherein the coating inhibits build-up of a fouling precipitate on the coated inner surface of the one or more reactors as compared to such build-up in the absence of the coating.

18 Claims, 4 Drawing Sheets

COATING TO INHIBIT FOULING OF REACTORS FOR CUMENE HYDROPEROXIDE CLEAVAGE

CROSS REFERENCE TO RELATED APPLICATIONS

This application is a 371 of International Application No. PCT/IB2015/056023, filed Aug. 7, 2015, which claims priority to Russian Application No. 2014132768, filed Aug. 8, 2014 which are incorporated herein by reference in their entirety.

BACKGROUND

A well-known method for the production of phenol and acetone by oxidation of cumene with atmospheric oxygen, followed by the acid-catalytic decomposition of cumene hydroperoxide, permits both end products to be produced with high yield (see, for example, Kruzhalov B. D., Golovanenko B. N., Combined Production of Phenol and Acetone, Moscow, Goskhimizdat, 1964, or Kirk-Othmer Encyclopedia of Industrial Chemistry). The method is widely used to produce these products and is the principal technique used in world practice.

Strategies for increasing productivity in processes for the conversion of cumene hydroperoxide to phenol and acetone include reduction of unwanted side products. Methods are known for producing phenol and acetone in which, to reduce the yield of phenol tar, cumene oxidation products containing cumene hydroperoxide (CHP), cumene, and dimethylbenzyl alchohol (DMBA) are cleaved in the presence of sulfuric acid. In a first stage, at a temperature of 55 to 80° C., most of the CHP (97 to 99%) is decomposed and dicumyl peroxide (DCP) is produced from DMBA and CHP. In a second stage, acetone is added at a temperature from 80 to 146° C. to the obtained reaction mixture containing phenol, acetone, dimethylbenzyl alcohol (DMBA) and dicumyl peroxide (DCP). The addition is made in an amount of 1.5 to 1.8 times the original concentration of acetone. Water is also added. In some cases the acid is partially neutralized with ammonia before the second separation stage in order to ensure optimal acidity of the catalyst. After breakdown of DCP formed in the first stage, decomposition of the remaining CHP and dehydration of the remaining DMBA occur at a temperature from 80 to 146° C.

While strategies directed to increased productivity by producing higher yields of desired products are known in the art, commercial processes for the decomposition of cumene hydroperoxide still result in a build-up of a fouling precipitate which can coat interior surfaces of reactors. This build-up of unwanted precipitate or residue results in operational problems and decreased productivity. There is a need in the art for a process that, in addition to producing high yields of desired products, avoids build-up of unwanted precipitates in the production equipment.

SUMMARY

In some embodiments, the disclosure concerns methods comprising: (a) decomposing a CHP to form phenol and a ketone and reaction of CHP with DMBA, both in the presence of a catalyst mixture to form a dicumyl peroxide (DCP) mixture in a first stage, wherein the first stage occurs in a first system comprising one or more reactors; and (b) forming a phenol, acetone, and AMS mixture from decomposition of the dicumyl peroxide (CHP) mixture formed in the first stage in a second stage, wherein the second stage occurs in a second system comprising one or more reactors; wherein the first and the second systems are connected in series, wherein the one or more reactors systems of the second system has a coating on at least a portion of an inner surface of the one or more reactors; and wherein the coating inhibits build-up of a fouling precipitate on the coated inner surface of the one or more reactors of the second system as compared to such build-up in the absence of the coating.

In certain embodiments, the disclosure concerns methods comprising forming a phenol and acetone mixture from the decomposition of a dicumyl peroxide mixture in a system comprising one or more reactors where at least a portion of an inner surface of the one or more reactors has a coating; wherein the coating inhibits build-up of a fouling precipitate on the coated inner surface of the one or more reactors as compared to such build-up in the absence of the coating.

In other embodiments, the disclosure concerns methods comprising: applying a coating to at least a portion of an inner surface of one or more reactors to form a coated surface wherein the coating minimizes chemical and physical interactions with component of the decomposition reaction; and wherein the one or more reactors are used in a two stage formation of phenol and acetone from cumene hydroperoxide mixture, and substantially no fouling precipitates are present on the coated surface at the second stage during an operation time from about 80 hours to about 16000 hours.

In yet other embodiments, the disclosure concerns systems comprising one or more reactors comprising an inner surface, wherein at least a portion of the inner surface has a coating, wherein the coating has a surface energy such that chemical and physical interactions with formed phenol are minimized, and wherein the system is used for a high throughput two stage method of formation of phenol and acetone from cumene hydroperoxide mixture.

BRIEF DESCRIPTION OF THE DRAWINGS

The accompanying figures, which are incorporated in and constitute a part of this specification, illustrate several aspects and together with the description serve to explain the principles of the disclosure.

Figure 1:
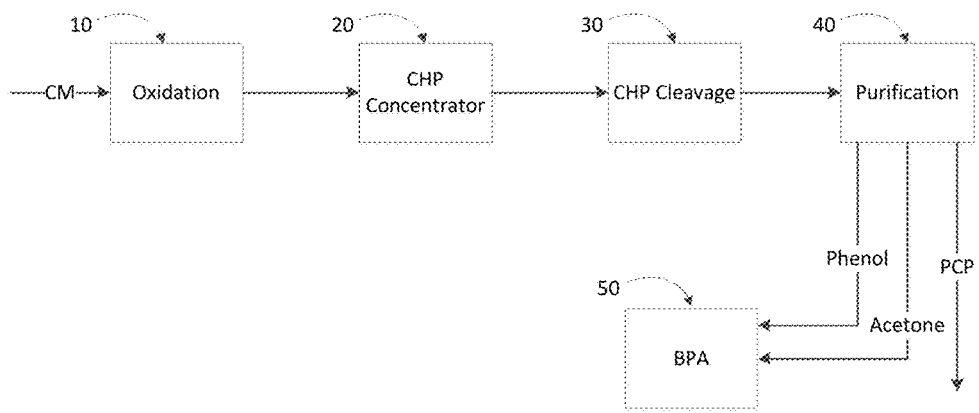
FIG. 1 depicts a schematic of a system for converting cumene to phenol and acetone.

Additional advantages of the disclosure will be set forth in part in the description which follows, and in part will be obvious from the description, or can be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

DETAILED DESCRIPTION

The present disclosure can be understood more readily by reference to the following detailed description of the disclosure and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present disclosure, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present disclosure is not entitled to antedate such publication by virtue of prior invention. Further, the dates of publication provided herein can be different from the actual publication dates, which can require independent confirmation.

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed. The term "about" is intended to include any standard deviation in the measurement of the value.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the disclosure as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the disclosure. Thus, if there are a variety of additional steps that can be performed it is understood that each of these additional steps can be performed with any specific embodiment or combination of embodiments of the methods of the disclosure.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

Although the specification may describe fouling precipitates in the context of cleavage equipment, fouling may affect other equipment during the conversion of cumene to phenol and acetone-cleavage mass contact, reactor, lines, bypass lines to online instrumentation, $2^{nd}$ stage dicumyl peroxide decomposition reactor, trim heaters, minimum flow line on pumps, and relief devices. Furthermore, the term "reactor" as used herein can comprise a vessel, reaction chamber, process conduit. Accordingly, the methods and systems described herein apply to other reactor/process equipment as well.

Fouling of cleavage equipment negatively impacts productivity of cumene hydroperoxide processes to produce phenol and acetone. While not wanting to be bound by theory, it is believed that at least one factor involved in fouling is an insoluble polymer precipitate or residue resulting from phenol condensation with minor aldehyde impurities present in the cleavage media. This fouling precipitate typically resembles brown "coffee grounds." For example, aldehydes formed by the oxidation of ethylbenzene, n-propylbenzene and formed in situ during the second stage of cleavage, react with phenol to produce insoluble "phenol-aldehyde" type resins.

Commercial cumene typically used in the phenol process contains impurities such as ethylbenzene and n-propylbenzene. These compounds are oxidized to their respective hydroperoxides and along with the cumene hydroperoxide formed in oxidation, pass together through concentration and on to cleavage. These peroxide impurities decompose in the CHP cleavage reactors forming acetaldehyde and propanal respectively. These are later partially removed in concentration and/or also in acetone fractionation.

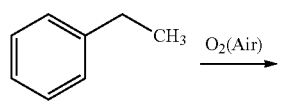

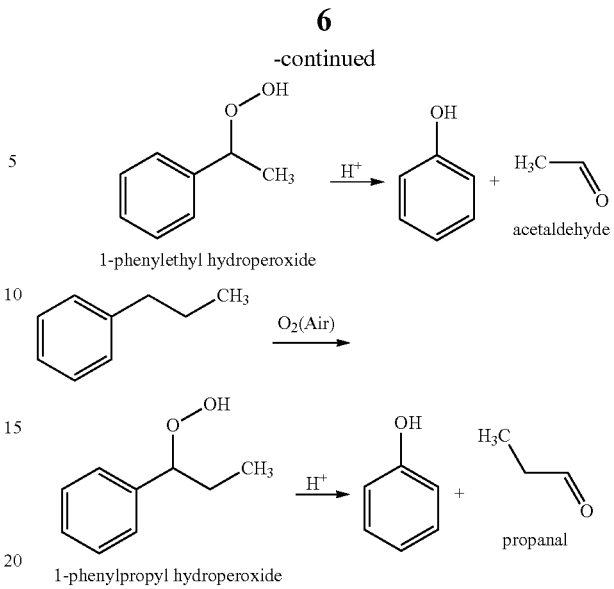

Aldehydes may also be formed in-situ in the cleavage area of the plant. Previous investigations into phenol-acetone process chemistry aimed at improving α-methylstyrene (AMS) cleavage yield have indicated that formaldehyde formation is possible via oxidation of AMS.

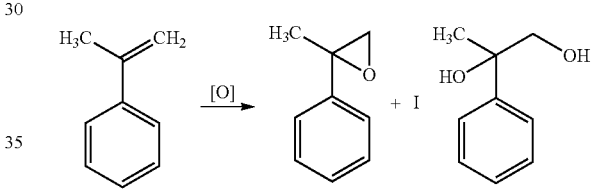

In the first step of this process, 2-Methyl-2-phenyloxirane forms when AMS reacts with the peroxides present under cleavage reaction conditions. 2-Methyl-2-phenyloxirane can be further hydrolyzed to 2-phenylpropane-1,2-diol in the presence of reaction media water. Both of these compounds can then further react with CHP in analogous reactions to DCP formation.

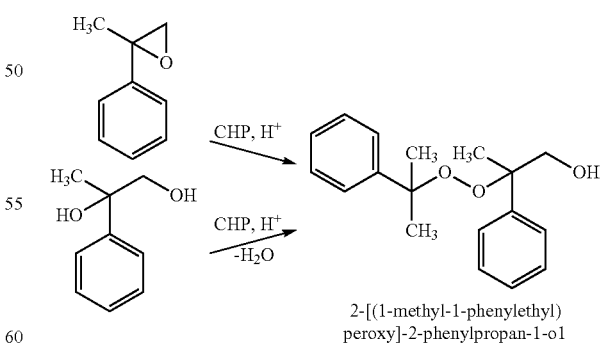

This oxygenated analog of DCP undergoes the same reactions as DCP, including reverse decomposition, hydrolysis, and finally, cleavage. These cleavage reactions can lead to intermediate products, which differ from the DCP cleavage intermediates by the presence of a hydroxyl group.

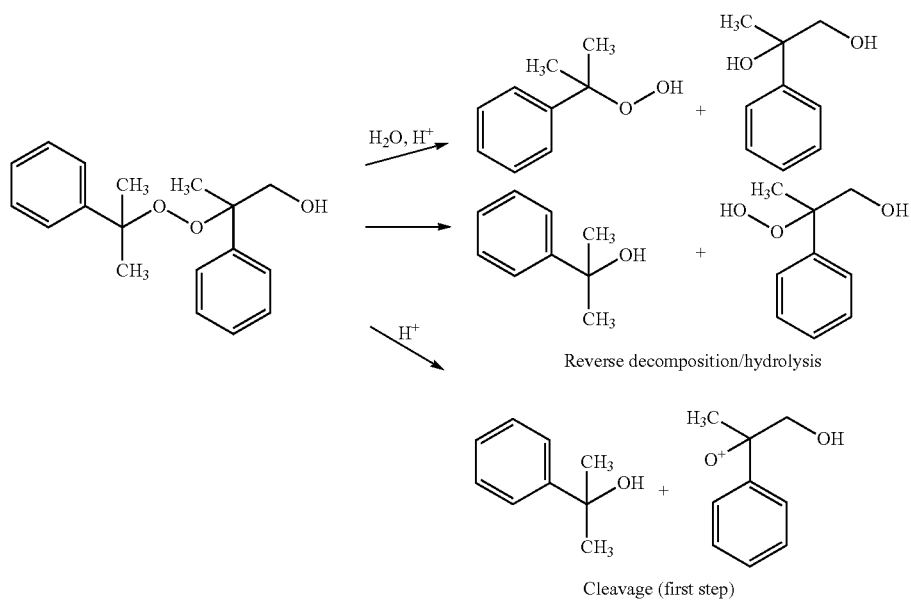

Reverse decomposition/hydrolysis

Cleavage (first step)

The relative migration rate for phenyl groups is known to be much faster than methyl groups. Thus, these reaction conditions result in the predominant formation of phenol and acetone rather than acetophenone and methanol in the case of CHP or DCP. The presence of the oxy-methyl group makes the situation different.

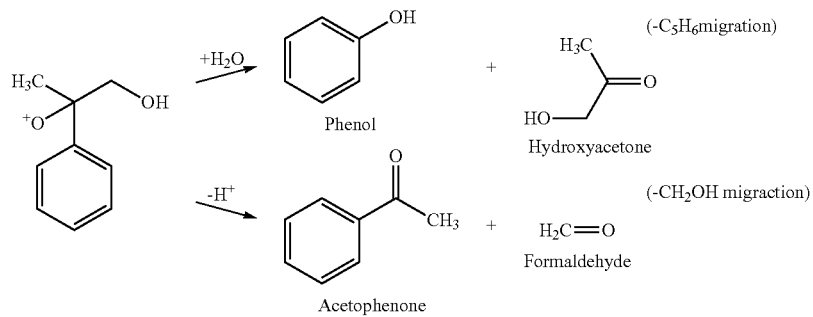

While investigating the mechanism for the formation of hydroxy-acetone (HA), it was found that the upper path of the above scheme does not take place under certain cleavage conditions. The oxy-methyl group migration to the electron deficient oxygen atom takes place faster than phenyl group migration. This results in minimal HA and phenol formation by this path while forming additional amounts of acetophenone accompanied with formaldehyde. This last reaction pathway is the most probable route for formaldehyde formation in cleavage. The presence of formaldehyde in cleavage can therefore be formed independently of the oxidation area. In addition, aldehydes carried through the process from oxidation or recycled from other areas of the plant can also form insoluble precipitates.

It should be noted that cleavage mass contains a large excess of phenol and acidic catalyst—satisfactory conditions for aldehyde condensation with phenol.

In addition to the formation of insoluble reaction products from formaldehyde and phenol, other reactions with formaldehyde are also possible. In the following scheme, the alkylation reaction is shown. In the first alkylation stage, the reaction between phenol and aldehydes is relatively slow. In the second stage, the alkylation of phenol by the benzyl alcohol formed in the first stage is much faster.

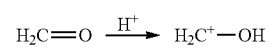

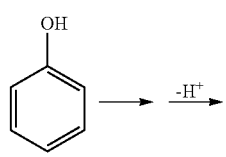

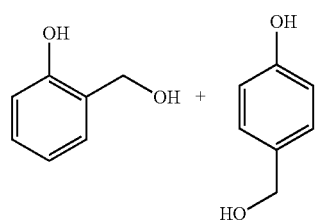

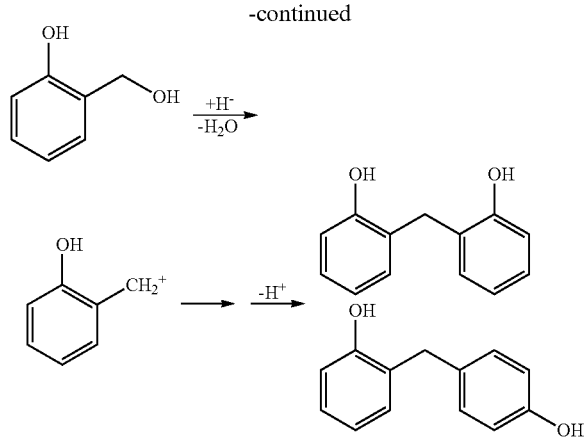

As a result, the main products of aldehyde reaction with phenol are bis-oxyphenyl methanes. These products are highly soluble in the reaction media and don't form precipitates as they are continuously removed from the reactor with the cleavage products. Thus, the precipitate formation is thought to be caused by other impurities. The likelihood for further alkylation(s) of these compounds with additional molecules of aldehydes has a low probability due to the large excess of phenol present in the reaction media.

However, the opportunity for "poly" condensation products that may result in insoluble precipitates is not completely eliminated. For example, condensation reactions may occur in a surface coordinated fashion in cleavage reactors as shown below.

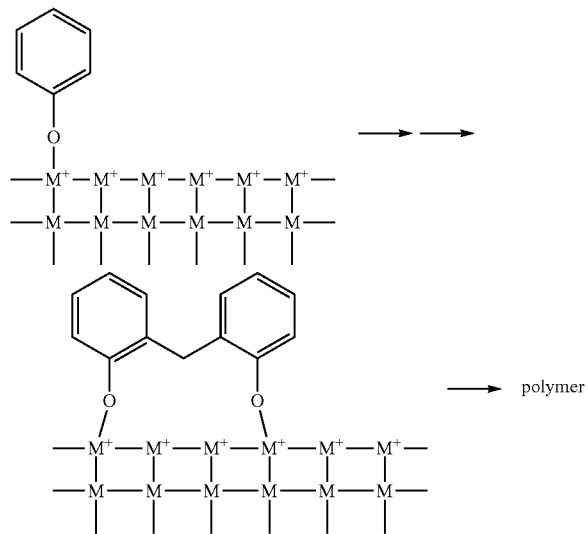

Phenol molecules when associated on a metal surface have a negative charge because of phenate formation with free valence on the surface metal atom. This further activates the phenol molecule towards electrophilic addition reactions, such as alkylation. Condensation of the absorbed intermediates with additional phenol molecules can lead to a "poly-anchored" particle depending on the extent of reaction that is then more reactive toward further alkylation and not readily removed from the reaction zone.

These hypotheses are also consistent with the observations made in the plant. Reaction products that result as a single condensation are expected to pass through the cleavage area without accumulation. "Poly"-condensation products, especially those potentially formed on the metal surfaces present in the cleavage equipment, would be expected to accumulate as evidenced in plant operation.

These mechanisms were tested in a laboratory scale cleavage apparatus having materials of construction matching those found in the commercial cleavage unit (see Examples). In addition, cleavage reactions were carried out where the metal surfaces of the reaction equipment was modified through the use of various coatings to study their effect on equipment fouling.

It appears that phenolic materials "anchored" over bare steel surfaces are the most probable cause of bulk "precipitate" formation. Accordingly, it has been found that use of inert surfaces that are unable to adsorb phenolic compounds can inhibit, and in certain cases eliminate, fouling of equipment in the cleavage area of the plant. In some embodiments, materials are used such that the coating has a surface energy of from about 19 to about 31 milliNewtons per meter (mN/m). Some preferred coating materials comprise fluorocarbon resin (such as fluoro-chlorocarbon resin and fluorinated ethers), polypropylene resin, polyethylene resin, and combinations comprising at least one of the foregoing. For example, the coating materials can be fluorocarbon resin. For example, the coating materials can be fluoro-chlorocarbon resin, fluorinated ethers, or a combination comprising at least one of the foregoing. In some embodiments, materials for coating surfaces to render them inert include polytetrafluoroethylene (PTFE) and PTFE based coatings.

In view of this background, the "fouling precipitate" described herein refers to the unwanted material that builds up within the reactor over time (also referred to as "precipitate"). This material typically comprises a polymeric material that results from unwanted side reactions during the decomposition of dicumyl peroxide process. At least a portion of the polymer is believed to result from the reaction of phenolic compounds with various aldehydes. The precipitate is insoluble in the reaction media and is often brown in color.

The fouling precipitate will accumulate or build-up within the reactor. The precipitate tends to coat on the inner surface of the reactor. In some embodiments, the precipitate appears to be anchored to the reactor's inner surface. Over time, the build-up of the precipitate can cause increased pressure drop across the reactor due to reduced flow or can even essentially completely block the flow of reactants through the reactor or a part of the reactor system. In some embodiments, the undesired build-up threshold within the reactor can occur when the internal diameter of the reactor reaches 70% or less, 50% or less, 30% or less, or 20% or less of the non-occluded internal diameter at any point within the reactor. In an extreme situation, the flow within the reactor may be completely blocked by the internal diameter approaching 0%.

In certain embodiments, a coating, typically a polymer coating, is applied to the reactor, typically the inner surface of the reactor that contacts the reactants, and inhibits the build-up of the fouling precipitate on the coated surface of the reactor as compared to such build-up in the absence of the coating. CHP decomposition reactor system parts including a coating to prevent build-up of the "brown precipitate" demonstrate resistance to fouling; inspection of test areas on a quarterly basis indicates that after 2 and 3 quarters no fouling is evident.

Systems

In some aspects, the disclosure concerns systems comprising one or more reactors comprising an inner surface, wherein at least a portion of the inner surface has a coating, wherein the coating has a surface energy such that chemical and physical interactions with formed phenol are minimized, and wherein the system is used for a high throughput two stage method of formation of phenol and acetone from cumene hydroperoxide. In the context of this disclosure, "minimized" means reduced to the smallest degree possible. For example, in some embodiments, the chemical and physical interactions are less than 20%, less than 10%, or less than 5% of that found with an uncoated surface. The term "high throughput" is typically associated with a system where at least 80% yield is accomplished at steady state.

In one aspect, the disclosure concerns systems comprising: (i) an oxidation reactor configured to receive a cumene feed and an oxidizing agent and to output a cumene oxidation product comprising cumene hydroperoxide; and (ii) a cleavage reactor configured to receive one or more of the cumene oxidation product and the converted cumene oxidation product, and to produce an output product comprising one or more of phenol, acetone, and alpha-methylstyrene.

An example of a schematic for accomplishing certain aspects of the disclosure is found in FIG. 1. Cumene is fed to an oxidation reactor 10 to produce a cumene oxidation product comprising cumene hydroperoxide (CHP) and dimethyl benzyl alcohol (DMBA). The cumene oxidation product is optionally fed to a CHP concentrator 20 to increase the concentration of CHP. The product of the oxidation reactor or the concentrator may be fed to the CHP cleavage reactor 30 where CHP is converted to a mixture comprising one or more of phenol, acetone and alpha-methylstyrene (which may be converted to paracumylphenol (PCP)). The product of the CHP cleavage rector may be purified (purifier 40) to isolate acetone and phenol. The acetone and phenol can then be fed to a Bisphenol-A (BPA) reactor 50 to produce BPA product.

Oxidation Reactor

In the first step of the cumene-to-phenol process, the cumene feed can enter an oxidation reactor (10). In one aspect, the oxidation reactor is configured to receive a cumene feed and an oxidizing agent. In another aspect, the oxidation reactor outputs a cumene oxidation product comprising cumene hydroperoxide and side products of cumene oxidation.

The oxidation reactor can circulate the cumene flow through a cascade of large bubble columns. In the bubble columns, the air is added at the bottom of each reactor and the oxygen can transfer from the air bubbles into the cumene. The oxidation reaction can be auto-catalyzed by the cumene hydroperoxide. The oxidation reactor can operate at pressures ranging from atmospheric to around 200 pounds per square inch (psi). The temperature of the oxidation reactor can range from 80° C.-130° C. The residence time in the reactor can range from 10 minutes to several hours.

The cumene feed can be produced, for example, from benzene and propylene. In one aspect, the cumene is produced commercially using a heterogeneous zeolite catalyst or an acid catalyst, for example, phosphoric acid and aluminum chloride.

The oxidizing agent can be any agent capable of oxidizing the cumene. In one aspect, the oxidizing agent is oxygen. The oxygen can be pure or as a mixture with other gases, for example the mixture of gases found in air. In another aspect, the oxidizing agent is air.

The cumene oxidation product comprises cumene hydroperoxide and dimethyl benzyl alcohol. The oxidation reactor can also output one or more by-products. The one or more by-products can include acetophenone (ACP) or methyl hydroperoxide (MHP) or a combination thereof.

In one aspect, the cumene oxidation product comprises from about 20 wt % to about 30 wt % cumene hydroperoxide and from about 0.1 wt % to about 2 wt % dimethyl benzyl alcohol.

Stripping Element

The system may optionally further comprise a stripping element (or CHP concentrator 20) in communication with the oxidation reactor, the stripping element configured to receive the cumene oxidation product and to modify a concentration of the cumene oxidation product, wherein the conversion reactor is configured to receive the modified cumene oxidation product. Typically the concentration of CHP would be increased in this element.

1$^{st}$ Stage Decomposition Reactor

The cleavage reaction in the manufacture of phenol and acetone from cumene is well known. In the system, a feed stream from the conversion reactor (CHP cleavage reactor 30) of the cumene oxidation product and the converted oxidation product passes into the cleavage reactor. An acid catalyst in the cleavage reactor decomposes the cumene oxidation product and the converted oxidation product into an output product comprising phenol, acetone, and alpha-methylstyrene, and other by-products.

In some embodiments, the cleavage takes place in a two reactor system. In a first system, comprising one or more reactors, cumene hydroperoxide is decomposed in the presence of a catalyst mixture to form phenol and a ketone. A portion of the CHP reacts with DMBA to form a dicumyl peroxide (DCP) mixture in a first stage. In a second stage, the product of the first stage can be fed to a second system (comprising one or more reactors) to form a phenol, acetone, and AMS mixture from decomposition of the dicumyl peroxide mixture formed in the first stage. As described herein, the first and the second systems are connected in series.

In certain embodiments, the second stage reaction is carried out at a temperature from about 90° C. to about 160° C. and a pressure from about 5 to about 200 psi.

In some aspects of the disclosure, the one or more cleavage reactors of the first or second system have a polymer coating on at least a portion of an inner surface of the one or more reactors. This coating inhibits build-up of a fouling precipitate, such as an insoluble phenol-aldehyde resin, on the coated inner surface of the one or more reactors as compared to such build-up in the absence of the coating. Given the conditions and tendency for fouling in the second stage of cleavage, the polymer coating is typically applied to the one or more reactors of the second system.

Use of inert surface coatings that are unable to adsorb phenolic compounds were found to inhibit and/or eliminate fouling of the cleavage equipment. Ideally, the surface should have little or no reactivity towards phenol. Some surfaces that meet these criteria have a surface energy such that chemical and physical interactions with phenol molecules are minimized Certain of these materials lead to a coating with a surface energy of from about 19 to about 31 mN/m. Some preferred coatings comprise a fluorocarbon resin, polypropylene resin, polyethylene resin, fluoro-chlorocarbon resin, fluorinated ethers or any combination thereof. Suitable fluorocarbon resins include polytetrafluoroethylene, copolymer of ethylene and chlorotrifluoroethylene, perfluoroalkoxy alkanes, or a combination thereof. In some embodiments, suitable materials for coating surfaces to render them inert include polytetrafluoroethylene (PTFE) and PTFE based coatings. One suitable coating is Teflon® (DuPont's brand of PTFE coating).

The polymer coating may be applied on the reactor inner surface by any suitable means. These means include film forming, mechanical attachment of "liners", spray coating, solution deposition, chemical vapor deposition, plasma deposition, electron beam, or any combination thereof. Such techniques are known to those skilled in the art. In some embodiments, the surface coating has a thickness from about 1 to about 10,000 μm. In other embodiments, the surface coating has a thickness from about 250-1000 μm and in other embodiments, 500-1000 μm.

The coating can be on any part of the reactor system that might experience fouling. For example, the coating may be on metal components such as tubing, a pipe, a pre-heater, a heat exchanger, a calorimeter, or any combination thereof. In some embodiments, the metal is stainless steel.

Advantageously, the coating will reduce unwanted precipitate buildup and, in some cases, ease the difficulty of cleaning and/or removing the coated equipment if precipitate does accumulate. In some embodiments, substantially no fouling precipitate is present on the inner coated surface of the one or more reactors in the second stage after an operation time of about 80 hours to about 16,000 hours. For example, no precipitate or only a small amount of precipitate is present. In some embodiments, the amount of precipitate present is such that less than 0.1, 1, 2, 3, 4, 5, or 10 percent of the reactor inner volume comprises the precipitate.

The coatings should be stable to process conditions present in the cleavage reactor. For example, the coatings should withstand exposure to pH values from about 1 to about 14 with substantially no cracking, swelling, pitting, or decomposition. Suitable coatings should also withstand exposure to a solvent with substantially no swelling. For example, in some embodiments, the amount of cracking, pitting, or decomposition present is such that less than: 0.01 10 percent (%), 1%, 2%, 3%, 4%, 5%, or 10% of the coating surface is cracked, pitted, or decomposed. In certain embodiments, the volume of the coating evidences no swelling or no more than: 0.01%, 1%, 2%, 3%, 4%, 5%, or 10% swelling by volume. In certain embodiments, the solvents include water, phenol, alpha methyl styrene, dimethyl benzyl alcohol, cumene hydroperoxide, dicumyl peroxide, acetophenone, acetone, or a combination comprising at least one of the foregoing.

The cleavage reaction can be extremely fast due to it exothermic nature and is essentially to completion in most processes. In one aspect, the cleavage reaction can occur within 30 seconds to 5 minutes. In fact it is common to use a constant boiling or refluxing type system for the isothermal cleavage reaction. This is generally the constant boiling temperature of the CHP decomposition product. Generally this can vary from about 70° to 90° C. Since this is the general cumene oxidation product and the converted oxidation product feed stream as well as the output product; the phenol to acetone molar ratio is essentially 1 to 1 throughout the course of the reaction. The ratio of acetone to phenol may be optionally increased depending on the amount of recycle acetone used to control the decomposition process.

The acid catalyst in the cleavage reactor can be any acidic material. To avoid corrosion, heavily corrosive inorganic acids, for example, hydrochloric acid or hydrobromic acid are not usually used in the cleavage reactor. Acid catalysts often used, but not limited to, include, for example, phosphoric acid or sulfuric acid or a combination thereof. In one aspect, the acid catalyst can be present in the quantity of about 10 to 3000 parts per million (ppm) of sulfuric acid per weight of composition mass.

In some embodiments, the cleavage reaction may be run in the presence of excess acetone. In this regard, the addition of recycle acetone may be used in the stream entering the cleavage reactor.

In some embodiments, these reactors have a specific surface not less than about 30 to 35 meter squared per ton ($m^2$/ton) of 100% CHP per hour. CHP conversion in the reactors in is 30 to 45%, 30 to 40%, or 10 to 30% when three reactors are utilized. In the event that more or less $1^{st}$ stage decomposition reactors are utilized, the % conversion will be different.

Other by-products that can be formed in the cleavage reactor include, for example, hydroxyacetone, 2-methylbenzofuran, or diacetone alcohol or a combination thereof. The by-products formed in the cleavage reactor can also include some aldehydes, for example, acetaldehyde.

The output product from the cleavage reactor can be cooled. In a further aspect, the output product can be neutralized in a neutralization unit to stop the acid-catalyzed reaction from the cleavage reactor. In one aspect, the output product can be neutralized using an neutralizing agent, such as sodium phenate.

Condensation Reactor

An optional condensation reactor (or BPA production reactor 50) may be configured to receive the output product and to produce one or more of Bisphenol A.

Purification System

The system may further comprise a purification system 40 that is configured to receive the output product and to purify the one or more of phenol, acetone, and alpha-methylstyrene to produce a purified output product. The purified output material may optionally be fed to a condensation reactor that is configured to receive the purified output product and to produce one or more of Bisphenol A and para-cumylphenol.

Methods

In some embodiments, the disclosure concerns methods comprising: (a) decomposing a cumene hydroperoxide in the presence of a catalyst mixture to form phenol and acetone and to react DMBA with CHP to form a dicumyl peroxide mixture (also containing phenol and acetone) in a first stage, and wherein the first stage occurs in a first system comprising one or more reactors; (b) forming a phenol, acetone, and AMS mixture from decomposition of the dicumyl peroxide mixture formed in the first stage in a second stage, and wherein the second stage occurs in a second system comprising one or more reactors; wherein the first and the second systems are connected in series, wherein the one or more reactors of the second system has a polymer coating on at least a portion of an inner surface of the one or more reactors; and wherein the coating inhibits build-up of a fouling precipitate on the coated inner surface of the one or more reactors of the second system as compared to such build-up in the absence of the coating.

Other embodiments concern methods comprising forming a phenol, acetone, and AMS mixture from decomposition of a dicumyl peroxide mixture in a system comprising one or more reactors where at least a portion of an inner surface of the one or more reactors has a coating; wherein the coating reduces formation of a fouling precipitate on the coated inner surface of the one or more reactors as compared to such formation in the absence of the coating.

Certain embodiments concern methods comprising applying a coating to at least a portion of an inner surface of one or more reactors to form a coated surface wherein the coating minimizes chemical and physical interactions with phenol molecules; and wherein the one or more reactors are used in a two stage formation of phenol and acetone from cumene hydroperoxide mixture, and substantially no fouling precipitates are present on the coated surface at the second stage for an operation time from about 80 hours to about 16000 hours.

Yet other embodiments concern methods comprising coating at least a portion of an inner surface of a reactor with a polymer coating, wherein the coating has a surface energy such that chemical and physical interactions with phenol molecules are minimized.

EXAMPLES

Detailed embodiments of the present disclosure are disclosed herein; it is to be understood that the disclosed embodiments are merely exemplary of the disclosure that may be embodied in various forms. Therefore, specific structural and functional details disclosed herein are not to be interpreted as limits, but merely as a basis for teaching one skilled in the art to employ the present disclosure. The specific examples below will enable the disclosure to be better understood. However, they are given merely by way of guidance and do not imply any limitation.

In an aspect, CHP cleavage experiments were carried out using a laboratory system operating under commercial process conditions.

Example 1: Second Stage Cleavage Reactor

The second stage cleavage reactor was originally constructed from a quarter inch (¼") SS316 tube formed into a coil having a volume of 8 milliliter (ml). The use of a process preheater was not required as the reaction coil was placed in an electrically heated aluminum block. This reactor has been observed to plug fully in approximately 3-4 months of operation (~30 hours/week). The reaction conditions in the second stage reactor were maintained between 125-135° C. and having a residence time in the heated zone of ~10 minutes. Most of the reactor fouling/plugging was observed to occur at the inlet to the reactor.

Example 2. Modified Cleavage Experimental Setup

Figure 2:
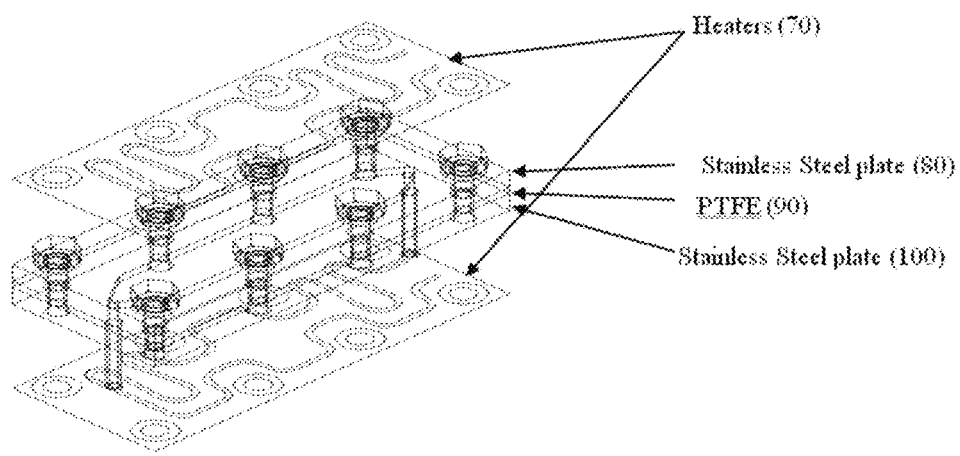
FIG. 2 is a schematic of a second stage cleavage reactor.

In order to investigate the formation of precipitates within the cleavage reactor, further testing was carried out using an alternatively designed second stage cleavage reactor as presented in FIG. 2 to provide experimental data for precipitate growth over the surface of the equipment, particularly the inner surface of the equipment that is in contact with the reactants.

This reactor consists of two stainless steel plates (80 and 100) separated with PTFE spacers (90) that provide 8 ml of internal volume as in the previous tubular reactor. Both plates were fitted with electric heaters (70) to provide equal and uniform heat input to the internal surfaces of the reactor. This design provided the opportunity to measure the quantity of precipitate and to test various surfaces for their ability to catalyze or prevent the formation/accumulation of fouling by-products. As this reactor has two equal heated surfaces, it is possible to compare the coating materials with respect to protection against fouling precipitates.

Example 3. PTFE vs. 316 Stainless Steel

The first series of experiments were carried out to test the effect of a PTFE vs. a stainless steel surface. This served as a test of the theory that "anchoring" of precipitate "growth centers" occurs over a metal surface. The choice of PTFE was made because of its chemical inertness and inability to form bonds with phenolic compounds combined with its chemical suitability for cleavage process conditions. One of the two second stage CHP cleavage step reactor walls was covered with a PTFE film (0.1 millimeter (mm)), while the remaining wall was "uncoated" bare metal. This construction allowed comparison of the precipitate formation over the two different surfaces under identical conditions. The surface area exposed to cleavage conditions was 13 cm$^3$/side.

PTFE Spray Coatings

The first PTFE based spray coating tested was Loctite 8192 (available from Henkel, Germany. Prior to coating, the surface of the second stage CHP cleavage reactor was mechanically cleaned and coated a total of 10 times with a thin film of Loctite 8192. Each layer was allowed to dry 30 minutes prior to application of the next layer.

The PTFE-coated reactor was assembled and installed into the laboratory cleavage unit as before. Testing of the coating was performed as previously performed with the stainless steel and PTFE film coated surfaces. After 100 hours of cleavage operation at 135° C. the reactor was disassembled and the surfaces inspected.

Vendor Supplied Commercial PTFE Coating Systems

Professional PTFE coatings were supplied by Rudolf Gutbrod GmbH of Dettingen/Erms, Germany Four different commercial coating systems were tested: (1) System C1 (continuous dry lubrication to reduce friction and increase durability; self-lubricating), (2) System DPL (multi-layer thermoplastic structure provides non-stick properties; mineral additives provide abrasion hardness), (3) System W1 (non-stick properties; no problems in operation and economically advantageous), and (4) System DR3 (said to be "mega durable"; optimized for durability; non-stick coating with hard undercoating; ceramic components provide system stability and abrasion resistance; a three-layer structure).

These samples were supplied on 30×75 mm (aluminum) plates. These samples were mounted into a modified CHP second stage cleavage reactor (FIG. 3) and were tested for 100 hours under standard CHP cleavage conditions: the first stage cleavage reaction was carried out at 50° C. utilizing 180 ppm H$_2$SO$_4$. The second stage cleavage reaction was carried out with partially neutralized sulfuric acid and the cleavage mass diluted with acetone. The second stage reactor was maintained at 135° C. The area of tested coating open to reaction mass contact was 10 square centimeters (cm$^2$).

Figure 3:
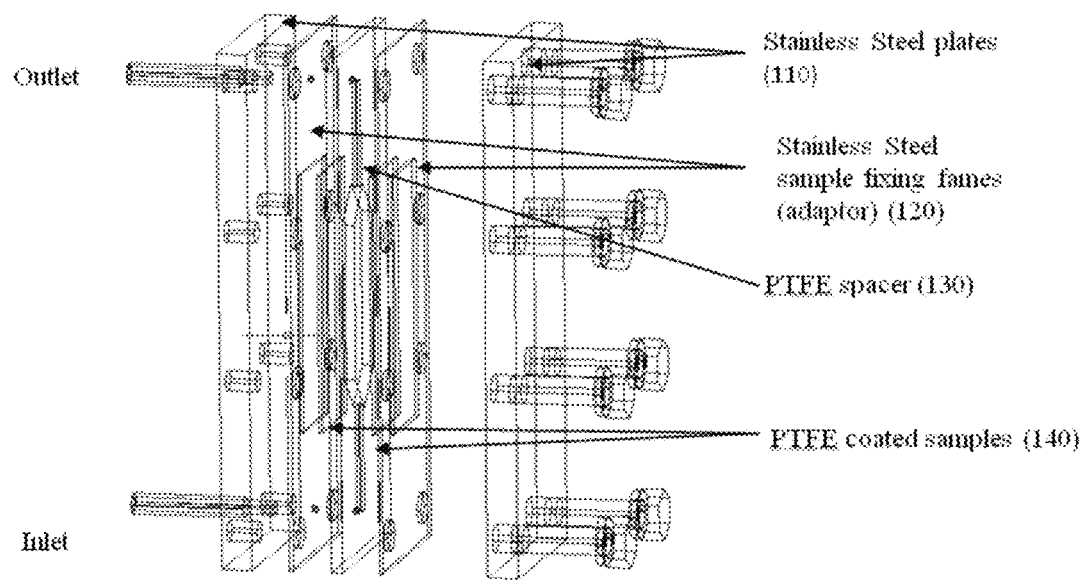
FIG. 3 is a schematic of a second stage cumene hydroperoxide reactor design for 30×75 mm sample testing.

Two samples were installed simultaneously on both sides of the spacer opening as shown in FIG. 3. Additional PTFE film seals were set to prevent reaction mixture leaks between the steel plates. The area of the coated surface was slightly reduced compared to earlier experiments with PTFE and spray coatings. The reduced size was the result of the size of available test plaques used.

Example 3. Graphite Materials

Graphite is a non-metallic material which is useful for constructing heat exchanging equipment. It is unable to coordinate phenol molecules as a steel surface does, but being of poly-aromatic structure, it may possibly adsorb phenolic compounds on the surface. Testing of graphite samples under CHP cleavage conditions was carried out to determine the suitability of graphite as a construction material for cleavage equipment, e.g. E-287, or for heat transfer in the second stage cleavage reaction equipment.

Soft Graphite

The graphite sample tested was a piece of plate used for the process of arc welding in an argon atmosphere and not designed for general chemical applications. Accordingly, this sample was evaluated as a preliminary test only.

Pure Graphite

Figure 4:
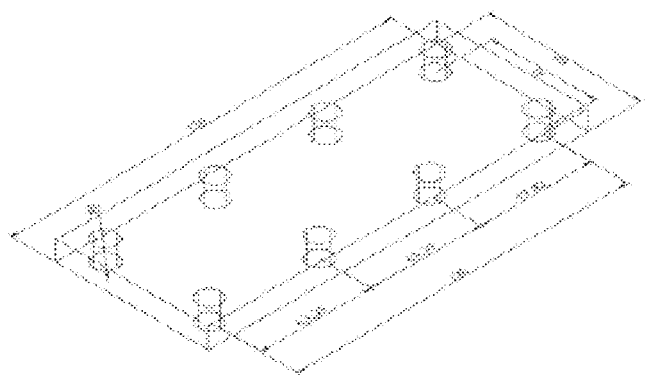
FIG. 4 depicts a graphite plate used in the construction of a heat exchanger.

This material is typically used as a base material for construction of heat exchangers for use in the chemical industry. The material used for testing was supplied as prefabricated plates according to FIG. 4 and installed into the lab CHP cleavage reactor. The material was supplied by Cepic (Compagnie d'Exploitation des Procédés Industriels Carbomeca) of Deville les Rouen, France.

Example 4. Phenolic Resin Impregnated Graphite

This material is typically used to construct heat exchangers for the chemical industry. In addition to the above pure graphite, it contains polymeric materials to improve the mechanical properties of the base material. The material used for testing was supplied by Cepic. These samples were machined to allow installation as part of a second stage cleavage reactor.

Each of the various graphite forms was installed in the test CHP decomposition reactor and tested for a period of 100 hours under standard CHP decomposition conditions: The first stage decomposition reaction was carried out at 50° C. utilizing 180 ppm $H_2SO_4$. The second stage decomposition reaction was carried out with the sulfuric acid catalyst partially neutralized and the decomposition mass diluted with acetone. The second stage reactor was maintained at 135° C. The area of tested coating open to reaction mass contact was 10 $cm^2$.

Examples 1-4: Results & Discussion

Figure 5:
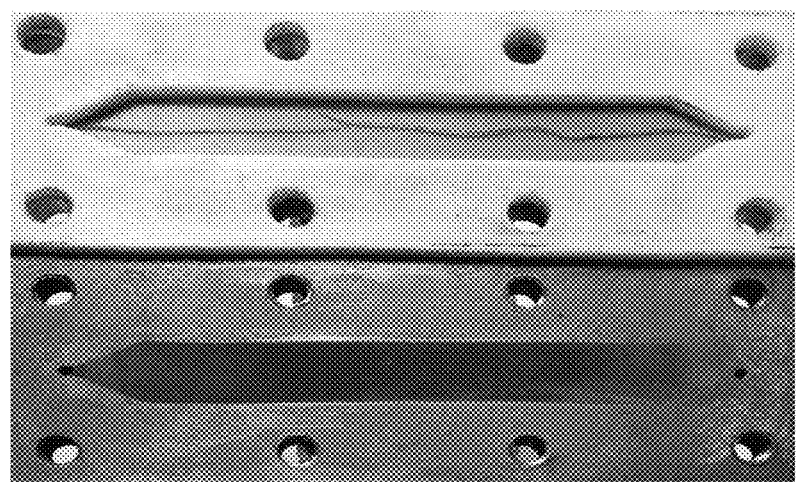
FIG. 5 depicts an uncoated and coated plate from a second stage cleavage reactor after 112 hours of operation.

Upon opening the second stage cleavage reactor after 112 hours of operation, there was clear evidence of a brown precipitate formation over the metal surface, while the opposite PTFE (Teflon™) surface remained almost completely free from precipitate (FIG. 5). Careful observation of the PTFE surface reveals that some brown precipitate particles are present, but only at the defects or scratches. In contrast, the metal surface was completely covered with brown precipitate. The precipitate was scraped off and collected from the surface and weighed 8.9 mg, yielding a phenol-formaldehyde film of approximately 10 µm in thickness. This corresponds to a growth rate of approximately 2 µm/day (starting from bare metal).

Figure 6:
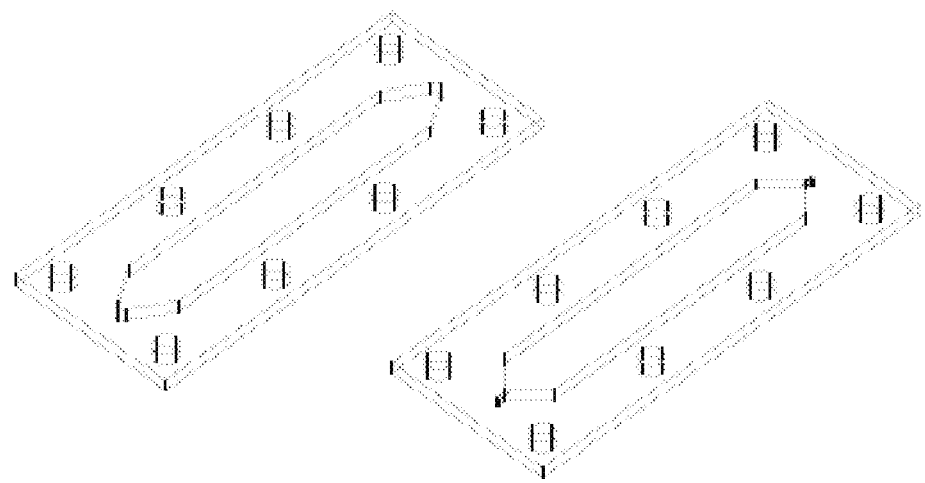
FIG. 6 is a depiction of spacer elements used in a second stage cleavage reactor.
Figure 7:
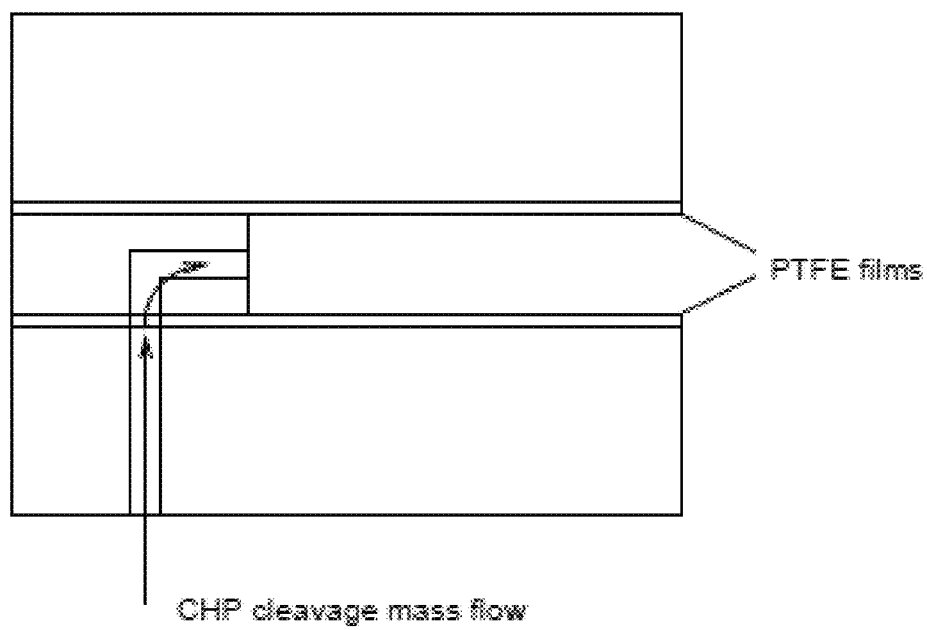
FIG. 7 depicts the CHP cleavage mass flow in a modified spacer design.

This experiment demonstrated an inhibition of the fouling precipitate by utilizing PTFE and like material coatings. The presence of fouling precipitate over the surface of coating may also be initiated by transfer of the "growth centers" from the metal surface to the coating defects. To test this thought, additional experiments were carried out where all of the reaction surfaces were constructed from or coated with PTFE materials. This required modification of the reactor spacer as shown below in FIGS. 6 and 7.

The modified reactor was again used in CHP cleavage testing for a period of 100 hours. The test reactor was then disassembled and examined. The reactor surfaces are not fouled with precipitate. In fact, even the PTFE surfaces are free of any precipitate. The results of these experiments indicate that such coatings, providing they can withstand the rigors of an industrial chemical plant, are able to eliminate fouling of the second stage cleavage reactors over long periods of time such as 80 to 16,000 hours, or longer. Coating of the second stage cleavage reactors using existing technologies currently available in the market should not influence the existing adiabatic second stage cleavage process.

The same approach may also be applied to other cleavage process equipment, including heat-exchangers, as well as other processing equipment where fouling may be an issue. In the case of heat exchangers, the thermal efficiency will only be slightly downgraded initially due to the insulating effect of the coating. An uncoated or "un-protected" exchanger would soon exceed these thermal efficiency losses as the thickness of the fouling coating increases. The fouling precipitate layer tends to continue to grow as the phenolic fouling resin is a "live" polymer, growing sequential polymeric chains, layer upon layer. Each aromatic ring can react with (form)aldehyde and the next phenol molecule, producing linear and/or branched polymer structures. Each branch adds additional reactive sites, thus increasing the formation rate for the precipitate with the increasing build-up.

The formation rate will increase to the point where it will be limited by the amount of aldehydes present in the cleavage mass. A value of 2 micrometers per day (µm/day) is a minimum estimated value, which in turn will result in a minimum of approximately (~) 60 micrometers per month (µm/month) of fouling film. Since protective PTFE films are on the order of 50 µm, thermal efficiency parity is achieved at ~1 month.

PTFE Spray Coating Tests

Spray coatings with PTFE based materials may be used. Depending on the quality these coatings and their application, the coatings should provide inhibition of fouling precipitate. The inhibition level may change to the extent there may be defects or thickness inconsistencies.

For example, the reactor coated with Loctite 8192 showed improved results when compared to bare metal, yet not as ideal as a solid PTFE film.

It was observed that some precipitate was still formed over the surface of the cleavage reactor. The amount was significantly reduced when compared to bare metal. The adhesion to the surface was also weak, allowing the precipitate to be easily removed. It was evident that most of the brown precipitate formed over either the metal surface or defects in the protective coating.

In summary, the experiments indicate that using a PTFE based coating is effect in inhibiting the formation and accumulation of fouling precipitate in the cleavage equipment.

Vendor Supplied Commercial PTFE Coating Systems

A number of professionally made coatings samples were obtained from Rudolf Gutbrod GmbH.

Two of the tested Rudolf Gutbrod GmbH coatings showed positive results, System DR3 and DPL. System C1 and W1 did not appear to be applicable for CHP cleavage process conditions. It should be noted that both DR3 and DPL coatings contain mineral components which may explain some brownish bloom appearing on the surface after testing, while the remainder of the surface remains clean and glossy. Optimum formulation should not contain mineral components as they may interact with phenol. Each of the test samples were tested under cleavage conditions for ~100 hours. Each of the coating plaques was weighed before and after testing and the results recorded in Table 1 below. From these results, it is evident that System W1 is not suitable for cleavage process conditions. System W1 was the only coating to lose mass during the testing period.

The mass information shown in Table 1 is a summary of the mass of the plaque and the coating. Tests may also be done by determining the mass of the coating itself independent of the metal plaque. Moreover, vacuum drying the test plaques after testing could also be part of the testing. For example, any mass loss measured between the post test results and post drying results could be correlated to solvent uptake into the coating. A coating that resists swelling in cleavage mass solvents would be expected to be more effective and suitable.

TABLE 1

Summary of mass changes for vender supplied coatings

|  | System C1 | System W1 | System DR3 | System DPL |
| --- | --- | --- | --- | --- |
| Initial Mass (g) | 5.9370 | 5.9860 | 6.1536 | 6.1516 |
| Final Mass (g) | 5.9566 | 5.9601 | 61641 | 6.1593 |
| Difference (g) | +0.0196 | −0.0259 | +0.0105 | +0.0077 |
| % difference | 0.33 | −0.43 | 0.17 | 0.13 |

System W1

Significant loss of coating was evidenced. Pieces of green material were observed during the first several hours of the test run in the product vessel. The base of the coating was damaged and visible cracking was observed.

System DR3

Minimal damage to the coating was observed. Two small areas of the coating were damaged during installation and assembling, but these areas were not located in the area open to the reaction mass. The substrate (aluminum) was attacked by the reaction media and showed some mineral reaction or "bloom."

A slight brownish bloom over the open reaction area was observed. If it is assumed that the mass change in the coating was correlated with this coating, it would correspond to a film of approximately 10 µm thickness.

System DPL

Practically no damage to coated surface was observed. There were minor swelling/pits (about 0.1 mm in size) observed on the area open to reaction mass. As with DR3, a slight brownish bloom was observed on the open area corresponding to an approximately 7 µm film.

System C1

Obvious coating damage was observed.

Both DR3 and DPL coating systems showed positive results for use in the CHP cleavage system.

Graphite Materials

The graphite materials tested were unexpectedly poor in their suitability for use in the cleavage area of the plant. This may be due to the nature/quality of the graphite used for the tests or it may be an intrinsic property of graphite. Graphite has been used in the chemical industry for many aggressive applications successfully. However, under CHP decomposition conditions, the graphite samples tested had less than optimum results.

Minor fouling was present on the surface. Surprisingly, however, the surface itself was damaged; the surface was covered with small domains that had "swelled" resulting in a surface damaged with voids. It appears that the graphite material tested contains "pores" that allow process chemicals to penetrate the substrate. These chemicals may then react and expand the substrate causing damage. The fouling precipitate may also form inside the pores causing damage by expanding inside the pore.

Pure graphite supplied by Cepic was not tested. The sample was installed in the cleavage reactor but found to be exceedingly porous, passing the reaction mixture outside the pressurized reactor.

The phenolic resin impregnated graphite was obtained from heat-exchanger production. The sample was tested for 200 hours and examined twice during this period: first after 100 hours and second after 200 hours of operation in conditions of second stage CHP cleavage.

The rate of fouling precipitate formation was measured and observed to be about 0.9 mg/hr. This corresponds to a growth rate of 250 mg/hr/m², or an average thickness growth of about 5 µm/day.

When compared to a bare stainless steel rate of 1-2 µm/day average, the results for phenolic impregnated graphite are significantly worse than the current bare stainless steel used in the cleavage area. It should be noted these results are obtained with a surface that has already been exposed to the reaction media for 100 hours and have a fouling patina already present.

After the test period, observation of the graphite surfaces show that the formation of the fouling precipitate is not uniform over the complete surface of the graphite plate. This could be caused if the precipitate is a live polymer, growing mostly on its own surface.

This would also be true for phenol-aldehyde resins. Another consideration is the nature of the "phenolic resin" used as the impregnation material. For example, the nature of the materials used to impregnate the graphite may promote or act as initial growth sites for the fouling precipitate.

Additionally, it was observed that the brown precipitate will grow over itself. This can be readily avoided by making the surface non-reactive. For example, other types of impregnated graphites resistant to alkylation reactions and also resistant to phenol adsorption may be necessary.

Examples 1-4: Conclusions

Without wishing to be bound by theory, the nature of the fouling precipitate that results in significant fouling of the second stage plant and laboratory cleavage equipment stems from the reaction of aldehydes with phenol under acidic conditions to form "phenol-aldehyde" insoluble resins. Aldehydes are both formed in situ and carried into cleavage as impurities from oxidation.

Coating the cleavage process equipment can significantly inhibit or even practically eliminate the fouling altogether. For example, a spray coating such as Loctite 8192 showed improved performance when compared to bare metal currently employed in plant operations. Further improvements were seen in some commercially applied spray coatings. Optimum results were obtained with pure PTFE coatings.

Constructing cleavage reactor equipment from graphite was not as desired as expected. The graphite samples tested had issues with porosity and possibly acted as reaction initiators. Fouling rates appeared to be as much as five times worse with impregnated graphite compared to un-treated stainless steel surfaces.

Overall, a PTFE-based coating appears to stop the initiation and surface growth of the fouling precipitate. PTFE lined pipe, coated heat exchangers, and coated reactors show the ability to inhibit and/or practically eliminate the precipitate fouling of the process equipment. In an aspect, an existing process line for online instrumentation was replaced by a sample coated line and after about one year of use, the line was inspected (e.g., visual inspection) and again after about 1.5 years. In both inspections, no precipitate was found, as compared to the original process line, which would typically foul after about 4-6 weeks.

Aspects

Aspect 1. A method comprising:

(a) decomposing a cumene hydroperoxide in the presence of a catalyst mixture to form phenol and acetone and reacted CHP with DMBA to form a dicumyl peroxide mixture in a first stage, and wherein the first stage occurs in a first system comprising one or more reactors;

(b) forming a phenol, acetone, and AMS mixture from decomposition of the dicumyl peroxide mixture formed in the first stage in a second stage, and wherein the second stage occurs in a second system comprising one or more reactors;

wherein the first and the second systems are connected in series, wherein the one or more reactors of the second system has a polymer coating on at least a portion of an inner surface of the one or more reactors; and wherein the coating inhibits build-up of a fouling precipitate on the coated inner surface of the one or more reactors of the second system as compared to such build-up in the absence of the coating.

Aspect 2. The method of aspect 1, wherein the one or more reactors comprise a stainless steel tubing, a pipe, a pre-heater, a heat exchanger, a calorimeter, or any combination thereof.

Aspect 3. The method of aspect 1 or 2, wherein substantially no fouling precipitate is present on the inner surface of the one or more reactors in the second stage after an operation time of about 80 hours to about 16000 hours.

Aspect 4. The method of any one of aspects 1-3, wherein the fouling precipitate comprises an insoluble phenol-aldehyde resin.

Aspect 5. The method of any one of aspects 1-4, wherein the second stage is carried out at a temperature from about 90° C. to about 160° C.

Aspect 6. The method any one of aspects 1-5, wherein the second stage is carried out at a pressure from about 5 to about 200 psi.

Aspect 7. The method of any one of aspects 1-6, wherein the coating withstands exposure to pH values from about 1 to about 14 with substantially no cracking, swelling, pitting, or decomposition, preferably no cracking, swelling, pitting, or decomposition.

Aspect 8. The method of any one of aspects 1-7, wherein the coating withstands exposure to a solvent with substantially no swelling; preferably no swelling.

Aspect 9. The method of aspect 8, wherein the solvent comprises water, phenol alpha methyl styrene, dimethyl benzyl alcohol, cumene hydroperoxide, dicumyl peroxide, acetophenone, acetone, or any combination thereof.

Aspect 10. The method of any one of aspects 1-9, wherein the coating has substantially no reactivity towards phenol; preferably no reactivity towards phenol.

Aspect 11. The method of any one of aspects 1-10, wherein the coating comprises a surface energy such that chemical and physical interactions with phenol molecules are minimized Aspect 12. The method of any one of aspects 1-11, wherein the surface energy of the coating is from about 19 to about 31 mN/m.

Aspect 13. The method of any one of aspects 1-12, wherein the coating comprises a fluorocarbon resin, polypropylene resin, polyethylene resin, fluoro-chlorocarbon resin, fluorinated ethers or any combination thereof.

Aspect 14. The method of any one of aspects 1-13, wherein the fluorocarbon resin comprises polytetrafluoroethylene, copolymer of ethylene and chlorotrifluoroethylene, perfluoroalkoxy alkanes, or a combination thereof.

Aspect 15. The method of any one of aspects 1-14, wherein the coating is formed as a film, mechanical attachment of a "liner", by a spray coating technique, solution deposition, chemical vapor deposition, plasma deposition, electron beam, or any combination thereof.

Aspect 16. The method of any one of aspects 1-15, wherein the coating has a thickness from about 1 to about 10,000 μm.

Aspect 17. A method comprising forming a phenol, acetone, and AMS mixture from decomposition of a dicumyl peroxide mixture in a system comprising one or more reactors where at least a portion of an inner surface of the one or more reactors has a polymer coating;

wherein the coating reduces formation of a fouling precipitate on the coated inner surface of the one or more reactors as compared to such formation in the absence of the coating.

Aspect 18. The method of aspect 17, wherein the coating comprises a fluorocarbon resin, polypropylene resin, polyethylene resin, fluoro-chlorocarbon resin, fluorinated ethers, or any combination thereof.

Aspect 19. The method of aspect 17 or 18, wherein the coating has a thickness from about 1 to about 10000 μm.

Aspect 20. A method comprising:

applying a coating to at least a portion of an inner surface of one or more reactors to form a coated surface wherein the coating minimizes chemical and physical interactions with phenol molecules; and wherein the one or more reactors are used in a two stage formation of phenol and acetone from cumene hydroperoxide mixture, and substantially no fouling precipitates are present on the coated surface at the second stage for an operation time from about 80 hours to about 16000 hours.

Aspect 21. The method of aspect 20, wherein the coating comprises a fluorocarbon resin, polypropylene resin, polyethylene resin, fluoro-chlorocarbon resin, fluorinated ethers, or any combination thereof.

Aspect 22. The method of any of the preceding aspects, wherein the coating has a thickness from about 1 to about 10,000 micrometer (μm).

Aspect 23. A system comprising one or more reactors comprising an inner surface, wherein at least a portion of the inner surface has a coating, wherein the coating has a surface energy such that chemical and physical interactions with formed phenol are minimized, and wherein the system is used for a high throughput two stage method of formation of phenol and acetone from cumene hydroperoxide mixture.

Aspect 24. The system of aspect 23, wherein the surface energy of the coating is from about 19 to about 31 mN/m.

Aspect 25. The system of aspect 23 or 24, wherein the coating comprises a fluorocarbon resin, polypropylene resin, polyethylene resin, fluoro-chlorocarbon resin, fluorinated ethers, or any combination thereof.

Aspect 26. The system of anyone of aspects 23-25, wherein the coating has a thickness from about 1 to about 10000 um.

Aspect 27. The system of anyone of aspects 23-26, wherein the one or more reactors comprise a stainless steel tubing, a pipe, a pre-heater, a heat exchanger, a calorimeter, or any combination thereof.

Aspect 28. The system of anyone of aspects 23-27, wherein substantially no impurities are adhered to the process surfaces at the second stage for an operation time from about 80 hours to about 16000 hours.

Aspect 29. A method comprising:
coating at least a portion of an inner surface of a reactor with a polymer coating,
wherein the coating has a surface energy such that chemical and physical interactions with phenol molecules are minimized.

Aspect 30. The method of aspect 29, wherein the surface energy of the coating is from about 19 to about 31 mN/m.

Aspect 31. The system of aspect 29 or 30, wherein the coating comprises a fluorocarbon resin, polypropylene resin, polyethylene resin, fluoro-chlorocarbon resin, fluorinated ethers, or any combination thereof.

Aspect 32. The method of any one of aspects 1-33, wherein the coating withstands exposure to a reaction media for a time from about 100 to about 300 hours with no or substantially no swelling, cracking, pitting or decomposition.

Aspect 33. The method of any one of aspects 1-33, wherein the reaction media comprises an acidic environment, an alkaline environment, a solvent, or any combination thereof.

Aspect 34. The method of any one of aspects 1-33, wherein the acid environment comprises sulfuric acid.

Aspect 35. The method of any one of aspects 1-33, wherein the alkaline environment comprises an ammonia.

Aspect 36. The method of any one of aspects 1-33, wherein the solvent comprises water, acetone, or any combination thereof.

Aspect 37. A method comprising:
(a) decomposing a cumene hydroperoxide in the presence of a catalyst mixture to form phenol and acetone and reacting CHP with DMBA to form a dicumyl peroxide mixture in a first stage, and wherein the first stage occurs in a first system comprising one or more reactors;
(b) forming a phenol and acetone mixture from decomposition of the dicumyl peroxide mixture formed in the first stage in a second stage, and wherein the second stage occurs in a second system comprising one or more reactors;
wherein the first and the second systems are connected in series,
wherein the one or more reactors of the second system has a coating on at least a portion of an inner surface of the one or more reactors; and
wherein throughput production of phenol and acetone is at least 6 months longer without replacement or cleanout of a fouled pipe compared to a substantially identical method for production of phenol and acetone from cumene hydroperoxide in the absence of the at least a portion of the one or more reactors of the second system having the coating.

Aspect 38. A method comprising:
(a) decomposing a cumene hydroperoxide to form phenol and acetone and reacting CHP with DMBA in the presence of a catalyst mixture to form a dicumyl peroxide mixture in a first stage, and wherein the first stage occurs in a first system comprising one or more reactors;
(b) forming a phenol, acetone, and AMS mixture from decomposition of the dicumyl peroxide mixture formed in the first stage in a second stage, and wherein the second stage occurs in a second system comprising one or more reactors;
wherein the first and the second systems are connected in series,
wherein the one or more reactors of the second system has a coating on at least a portion of an inner surface of the one or more reactors; and
wherein throughput production of phenol and acetone is at least 6 months longer without undesired build-up such that the internal diameter of the reactor reaches 70% or less, 50% or less, 30% or less, or 20% or less of a non-occluded internal diameter at any point within the reactor.

Aspect 39. A method comprising:
(a) decomposing a cumene hydroperoxide to form phenol and acetone and to react CHP and DMBA in the presence of a catalyst mixture to form a dicumyl peroxide mixture in a first stage, and wherein the first stage occurs in a first system comprising one or more reactors;
(b) forming a phenol, acetone, and AMS mixture from decomposition of the dicumyl peroxide mixture formed in the first stage in a second stage, and wherein the second stage occurs in a second system comprising one or more reactors;
wherein the first and the second systems are connected in series, wherein the one or more reactors of the second system has a coating on at least a portion of an inner surface of the one or more reactors; and
wherein the coating inhibits formation of a fouling precipitate on the coated inner surface of the one or more reactors of the second system as compared to such formation in the absence of the coating.

It will be apparent to those skilled in the art that various modifications and variations can be made in the present disclosure without departing from the scope or spirit of the disclosure. Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed:
1. A method comprising:
(a) decomposing a cumene hydroperoxide to form phenol and acetone and to react cumene hydroperoxide with dimethylbenzyl alcohol in the presence of a catalyst mixture to form a dicumyl peroxide mixture in a first stage, wherein the first stage occurs in a first system comprising a reactor; and
(b) forming a phenol, acetone, and α-methylstyrene mixture from decomposition of the dicumyl peroxide mixture formed in the first stage in a second stage, wherein the second stage occurs in a second system comprising a reactor;
wherein the first and the second systems are connected in series,
wherein the reactor of the second system has a polymer coating on at least a portion of an inner surface of the reactor,
wherein a surface energy of the coating is from about 19 to about 31 mN/m, and
wherein the coating inhibits build-up of a fouling precipitate on the coated inner surface of the reactor of the second system as compared to such build-up in the absence of the coating.

2. The method of claim 1, wherein the reactor comprise a stainless steel tubing, a pipe, a pre-heater, a heat exchanger, a calorimeter, or any combination thereof.

3. The method of claim 1, wherein substantially no fouling precipitate is present on the inner surface of the reactor in the second stage after an operation time of about 80 hours to about 16,000 hours.

4. The method of claim 1, wherein the fouling precipitate comprises an insoluble phenol-aldehyde resin.

5. The method of claim 1, wherein the second stage is carried out at a temperature from about 90° C. to about 160° C.

6. The method of claim 1, wherein the second stage is carried out at a pressure from about 5 to about 200 psi.

7. The method of claim 1, wherein the coating withstands exposure to pH values from about 1 to about 14 with substantially no cracking, swelling, pitting, or decomposition.

8. The method of claim 1, wherein the coating withstands exposure to a solvent with substantially no swelling.

9. The method of claim 8, wherein the solvent comprises water, phenol alpha methyl styrene, dimethyl benzyl alcohol, cumene hydroperoxide, dicumyl peroxide, acetophenone, acetone, or any combination thereof.

10. The method of claim 1, wherein the coating has substantially no reactivity towards phenol.

11. The method of claim 1, wherein the coating is formed as a film, mechanical attachment of a "liner", by a spray coating technique, solution deposition, chemical vapor deposition, plasma deposition, electron beam, or any combination thereof.

12. A method comprising
forming a phenol, acetone, and α-methylstyrene mixture from decomposition of a dicumyl peroxide mixture in a system comprising reactor where at least a portion of an inner surface of the reactor has a polymer coating; wherein a surface energy of the coating is from about 19 to about 31 mN/m; and
wherein the coating inhibits build-up of a fouling precipitate on the coated inner surface of the reactor as compared to such build-up in the absence of the coating.

13. A method comprising:
applying a coating to at least a portion of an inner surface of reactor to form a coated surface wherein the coating minimizes chemical and physical interactions with phenol molecules; and
wherein the reactor are used in a two stage formation of phenol and acetone from cumene hydroperoxide mixture, and substantially no fouling precipitates are present on the coated surface at the second stage during an operation time from about 80 hours to about 16000 hours.

14. The method of claim 1, wherein the coating comprises a fluorocarbon resin, polypropylene resin, polyethylene resin, fluoro-chlorocarbon resin, fluorinated ethers or any combination thereof.

15. The method of claim 14, wherein the fluorocarbon resin comprises polytetrafluoroethylene, copolymer of ethylene and chlorotrifluoroethylene, perfluoroalkoxy alkanes, or a combination thereof.

16. The method of claim 1, wherein the coating has a thickness from about 500 to about 10,000 μm.

17. A system comprising reactor comprising an inner surface, wherein at least a portion of the inner surface has a coating, wherein the coating has a surface energy such that chemical and physical interactions with formed phenol are minimized, wherein a surface energy of the coating is from about 19 to about 31 mN/m, and wherein the system is used for a high throughput two stage method of formation of phenol and acetone from cumene hydroperoxide mixture.

18. The method of claim 1, wherein the coating has a thickness from about 500 to about 1,000 μm.

* * * * *